US007851671B2

(12) United States Patent
Takakura et al.

(10) Patent No.: US 7,851,671 B2
(45) Date of Patent: *Dec. 14, 2010

(54) DISEASE-RESISTANT PLANTS AND METHOD OF CONSTRUCTING THE SAME

(75) Inventors: Yoshimitsu Takakura, Shizuoka (JP); Yasuhiro Inoue, Ibaraki (JP); Shigeru Kuwata, Kanagawa (JP); Fumiki Tsutsumi, Kanagawa (JP); Yuji Ishida, Shizuoka (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/406,502

(22) Filed: Mar. 18, 2009

(65) Prior Publication Data

US 2009/0229011 A1    Sep. 10, 2009

Related U.S. Application Data

(63) Continuation of application No. 10/363,832, filed as application No. PCT/JP01/07785 on Sep. 7, 2001, now Pat. No. 7,525,014.

(30) Foreign Application Priority Data

Sep. 7, 2000    (JP) .............................. 2000-271413

(51) Int. Cl.
*A01H 5/00*     (2006.01)
*C12N 15/09*    (2006.01)
*C12N 15/82*    (2006.01)
*C12N 15/31*    (2006.01)

(52) U.S. Cl. ........................ 800/279; 800/278; 800/298; 800/288; 435/468; 435/419; 435/430.1

(58) Field of Classification Search ........................ None
See application file for complete search history.

(56) References Cited

U.S. PATENT DOCUMENTS

| | | | |
|---|---|---|---|
| 5,708,139 | A | 1/1998 | Collmer et al. |
| 5,850,015 | A | 12/1998 | Bauer et al. |
| 5,858,786 | A | 1/1999 | Collmer et al. |
| 5,866,776 | A | 2/1999 | Marie de Wit |
| 5,977,060 | A | 11/1999 | Zitter et al. |
| 5,981,843 | A | 11/1999 | Chappell et al. |
| 6,100,451 | A | 8/2000 | Chappell et al. |
| 6,342,654 | B1 | 1/2002 | Li et al. |
| 6,903,247 | B2 | 6/2005 | Aldwinckle et al. |
| 7,525,014 | B2 * | 4/2009 | Takakura et al. ............ 800/279 |

FOREIGN PATENT DOCUMENTS

| | | |
|---|---|---|
| EP | 1132400 A1 | 9/2001 |
| JP | 5-153978 A | 6/1993 |
| JP | 8-510127 A | 10/1996 |
| JP | 11-506938 A | 6/1999 |
| JP | 2000-175698 A | 6/2000 |
| WO | WO-94/26782 A | 11/1994 |
| WO | WO-96/36697 A | 11/1996 |
| WO | WO-96/39802 A1 | 12/1996 |
| WO | WO-00/14242 A1 | 3/2000 |
| WO | WO-00/20452 A2 | 4/2000 |
| WO | WO-00/28055 A2 | 5/2000 |
| WO | WO-01/21657 A1 | 3/2001 |
| WO | WO-02/072817 A1 | 9/2002 |

OTHER PUBLICATIONS

Gopalan et al., The Plant Cell, 1996, vol. 8, pp. 1095-1105.
Culver & Dawson, Molecular Plant-Microbe Interactions, 1991, vol. 4, No. 5, pp. 458-463.
Hammond-Kosack et al., The Plant Cell, 1996, vol. 8, pp. 1773-1791.
Sticher et al., Annu. Rev. Phytopathol., 1997, vol. 35, pp. 235-270.
Dangl et al., The Plant Cell, 1996, vol. 8, pp. 1793-1807.
Yang et al., Genes & Development, 1997, vol. 11, pp. 1621-1639.
Boller, Annu. Rev. Plant Physiol. Plant Mol. Biol., 1995, vol. 46, pp. 189-214.
Wei et al., Science, 1992, vol. 257, pp. 85-88.
Arlat et al., The EMBO Journal, 1994, vol. 13, No. 3, pp. 543-553.
Charkowski et al., J. Bacteriology, 1998, vol. 180, No. 19, pp. 5211-5217.
Bauer et al., MPMI, 1995, vol. 8, No. 4, pp. 484-491.
Cui et al., MPMI, 1996, vol. 9, No. 7, pp. 565-573.
He et al., MPMI, 1994, vol. 7, No. 2, pp. 289-292.
Desikan et al., Biochem J., 1998, vol. 330, pp. 115-120.
Desikan et al., J. Exp. Bot., 1998, vol. 49, No. 327, pp. 1767-1771.
Desikan et al., Planta, 1999, vol. 210, pp. 97-103.
Dong et al., The Plant Journal, 1999, vol. 20, No. 2, pp. 207-215.
Strobel et al., The Plant Journal, 1996, vol. 9, No. 4, pp. 431-439.
Taniguchi et al., Plant Cell Physiol., 2000, vol. 41, No. 1, pp. 42-48.
Yamada et al., Plant Cell Physiol., 1994, vol. 35, No. 6, pp. 917-926.
Kawamata et al., Plant Cell Physiol., 1997, vol. 38, No. 7, pp. 792-803.
Komari et al., The Plant Journal, 1996, vol. 10, No. 1, pp. 165-174.
Lee et al., The Plant Cell, 2001, vol. 13, pp. 1079-1093.
Takakura et al., Ikushugaku Kenkyu, 2002, vol. 4, Suppl. 2, p. 293.
Takakura et al., Abstracts of the Phytopathological Society of Japan—Annual Meeting, 2003, No. 182.
Gail Preston et al., Molecular Plant-Microbe Interactions, 1995, vol. 8, No. 5, pp. 717-732. (XP000918614).
Sheng Yang He et al., Cell, 1993, vol. 73, pp. 1255-1266. (XP002914570).
Li Rugang et al., Science in China (Series C), 1999, vol. 42, No. 1, pp. 96-101. (XP009041030).
US 5,650,387, 07/1997, Wei et al. (withdrawn)

* cited by examiner

*Primary Examiner*—Medina A Ibrahim
(74) *Attorney, Agent, or Firm*—Birch, Stewart, Kolasch & Birch, LLP (57) ABSTRACT

The present invention provides transgenic, disease-resistant plants which have been transformed with an expression cassette including a constitutive gene expression promoter; and a gene, under the control of the promoter, encoding a harpin. The transformed cells in the transgenic plant effect the constitutive expression of the harpin in an amount effective for inducing a defense reaction. The harpin is a protein consisting of an amino acid sequence that is at least 90% homologous to the amino acid sequence of SEQ ID NO: 2, and possesses a hypersensitive-response-inducing activity. The present invention also provides methods for producing the transgenic plants, expression cassettes, recombinant vectors and genes encoding harpins.

8 Claims, 4 Drawing Sheets

| Construct name | Inducible/ Constitutive | Contents of the construct | Plants which the construct was introduced |
|---|---|---|---|
| PALL-hrpZ | Inducible | PAL1.45 pro — hrpZ | Tobacco |
| PALS-hrpZ | Inducible | PAL0.45 pro — hrpZ | Tobacco |
| 35S-hrpZ | Constitutive | 35S pro — hrpZ | Rice, Tobacco |
| PPDK-hrpZ | Constitutive | PPDK pro — hrpZ | Rice, Tobacco |

Fig. 1  Constructs introduced into plants

Fig. 2  Expression of harpin$_{pss}$ in tobacco and rice

Fig. 3   Formation of hypersensitive-response-like localized necrosis spots

Fig. 4 Resistance to powdery mildew

```
                        SEQUENCE LISTING

<160> NUMBER OF SEQ ID NOS: 7

<210> SEQ ID NO 1
<211> LENGTH: 1029
<212> TYPE: DNA
<213> ORGANISM: Pseudomonas syringae pv. syringae LOB2-1

<400> SEQUENCE: 1 atg cag agt ctc agt ctt aac agc agc tcg ctg caa acc ccg gca atg      48
Met Gln Ser Leu Ser Leu Asn Ser Ser Ser Leu Gln Thr Pro Ala Met
1               5                   10                  15
```

```
gcc ctt gtc ctg gta cgt cct gaa acc gag acg act ggc gcc agt acg      96
Ala Leu Val Leu Val Arg Pro Glu Thr Glu Thr Thr Gly Ala Ser Thr
             20                  25                  30 tcg agc aag gcg ctt cag gaa gtt gtc gtg aag ctg gcc gag gaa ctg     144
Ser Ser Lys Ala Leu Gln Glu Val Val Val Lys Leu Ala Glu Glu Leu
         35                  40                  45 atg cgc aat ggt caa ctc gac gac agc tcg cca ttg ggc aaa ctg ctg     192
Met Arg Asn Gly Gln Leu Asp Asp Ser Ser Pro Leu Gly Lys Leu Leu
 50                  55                  60 gcc aag tcg atg gcc gcg gat ggc aag gca ggc ggt atc gag gat         240
Ala Lys Ser Met Ala Ala Asp Gly Lys Ala Gly Gly Gly Ile Glu Asp
 65                  70                  75                  80 gtc atc gct gcg ctg gac aag ctg att cat gaa aag ctg ggt gac aac     288
Val Ile Ala Ala Leu Asp Lys Leu Ile His Glu Lys Leu Gly Asp Asn
                 85                  90                  95 ttc ggc gcg tct gcg gac aac gcc tcg ggt acc gga cag cag gac ctg     336
Phe Gly Ala Ser Ala Asp Asn Ala Ser Gly Thr Gly Gln Gln Asp Leu
            100                 105                 110 atg act cag gtg ctc agt ggc ctg gcc aag tct atg ctc gat gat ctt     384
Met Thr Gln Val Leu Ser Gly Leu Ala Lys Ser Met Leu Asp Asp Leu
            115                 120                 125 ctg acc aag cag gat ggc ggg gca agc ttc tcc gaa gac gat atg ccg     432
Leu Thr Lys Gln Asp Gly Gly Ala Ser Phe Ser Glu Asp Asp Met Pro
        130                 135                 140 atg ctg aac aag atc gcg cag ttc atg gat gac aat ccc gca cag ttt     480
Met Leu Asn Lys Ile Ala Gln Phe Met Asp Asp Asn Pro Ala Gln Phe
145                 150                 155                 160 ccc aag ccg gac tcg ggt tcc tgg gtg aac gaa ctc aag gaa gac aac     528
Pro Lys Pro Asp Ser Gly Ser Trp Val Asn Glu Leu Lys Glu Asp Asn
                165                 170                 175 ttc ctt gat ggc gac gaa acg gct gcg ttc cgc tcg gca ctc gac atc     576
Phe Leu Asp Gly Asp Glu Thr Ala Ala Phe Arg Ser Ala Leu Asp Ile
            180                 185                 190 att ggc cag caa ctg ggt aat cag cag agt ggc gct ggc ggt ctg gcg     624
Ile Gly Gln Gln Leu Gly Asn Gln Gln Ser Gly Ala Gly Gly Leu Ala
            195                 200                 205 ggg acg ggt gga ggt ctg ggc act ccg agc agt ttt tct aac aac tcg     672
Gly Thr Gly Gly Gly Leu Gly Thr Pro Ser Ser Phe Ser Asn Asn Ser
        210                 215                 220 tcc gtg acg ggt gat ccg ctg atc gac gcc aat acc ggt ccc ggt gac     720
Ser Val Thr Gly Asp Pro Leu Ile Asp Ala Asn Thr Gly Pro Gly Asp
225                 230                 235                 240 agc ggc aat agc agt ggt gag gcg ggg caa ctg atc ggc gag ctt atc     768
Ser Gly Asn Ser Ser Gly Glu Ala Gly Gln Leu Ile Gly Glu Leu Ile
                245                 250                 255 gac cgt ggc ctg caa tcg gta ttg gcc ggt ggt gga ctg ggc aca ccc     816
Asp Arg Gly Leu Gln Ser Val Leu Ala Gly Gly Gly Leu Gly Thr Pro
            260                 265                 270 gta aac acc ccg cag acc ggt acg gcg gcg aat ggc gga cag tcc gct     864
Val Asn Thr Pro Gln Thr Gly Thr Ala Ala Asn Gly Gly Gln Ser Ala
            275                 280                 285 cag gat ctt gac cag ttg ctg ggc ggc ttg ctc aag ggc ctt gaa         912
Gln Asp Leu Asp Gln Leu Leu Gly Gly Leu Leu Lys Gly Leu Glu
        290                 295                 300 gcg acg ctc aag gat gcc ggt caa acc gct acc gac gtg cag tcg agc     960
Ala Thr Leu Lys Asp Ala Gly Gln Thr Ala Thr Asp Val Gln Ser Ser
305                 310                 315                 320
```

```
gct gcg caa atc gcc acc ttg ctg gtc agt acg ctg ctg caa ggc acc     1008
Ala Ala Gln Ile Ala Thr Leu Leu Val Ser Thr Leu Leu Gln Gly Thr
            325                 330                 335 cgc aat cag gct gca gcc tga                                          1029
Arg Asn Gln Ala Ala Ala
            340
```

<210> SEQ ID NO 2
<211> LENGTH: 342
<212> TYPE: prt
<213> ORGANISM: Pseudomonas syringae pv. syringae LOB2-1

<400> SEQUENCE: 2

```
Met Gln Ser Leu Ser Leu Asn Ser Ser Leu Gln Thr Pro Ala Met
1               5                   10                  15

Ala Leu Val Leu Val Arg Pro Glu Thr Glu Thr Gly Ala Ser Thr
                20                  25                  30

Ser Ser Lys Ala Leu Gln Glu Val Val Lys Leu Ala Glu Glu Leu
            35                  40                  45

Met Arg Asn Gly Gln Leu Asp Asp Ser Ser Pro Leu Gly Lys Leu Leu
50                      55                  60

Ala Lys Ser Met Ala Ala Asp Gly Lys Ala Gly Gly Ile Glu Asp
65                  70                  75                  80

Val Ile Ala Ala Leu Asp Lys Leu Ile His Glu Lys Leu Gly Asp Asn
                85                  90                  95

Phe Gly Ala Ser Ala Asp Asn Ala Ser Gly Thr Gly Gln Gln Asp Leu
                100                 105                 110

Met Thr Gln Val Leu Ser Gly Leu Ala Lys Ser Met Leu Asp Asp Leu
            115                 120                 125

Leu Thr Lys Gln Asp Gly Gly Ala Ser Phe Ser Glu Asp Asp Met Pro
130                     135                 140

Met Leu Asn Lys Ile Ala Gln Phe Met Asp Asp Asn Pro Ala Gln Phe
145                 150                 155                 160

Pro Lys Pro Asp Ser Gly Ser Trp Val Asn Glu Leu Lys Glu Asp Asn
                165                 170                 175

Phe Leu Asp Gly Asp Glu Thr Ala Ala Phe Arg Ser Ala Leu Asp Ile
            180                 185                 190

Ile Gly Gln Gln Leu Gly Asn Gln Gln Ser Gly Ala Gly Gly Leu Ala
        195                 200                 205

Gly Thr Gly Gly Gly Leu Gly Thr Pro Ser Ser Phe Ser Asn Asn Ser
210                     215                 220

Ser Val Thr Gly Asp Pro Leu Ile Asp Ala Asn Thr Gly Pro Gly Asp
225                 230                 235                 240

Ser Gly Asn Ser Ser Gly Glu Ala Gly Gln Leu Ile Gly Glu Leu Ile
                245                 250                 255

Asp Arg Gly Leu Gln Ser Val Leu Ala Gly Gly Leu Gly Thr Pro
            260                 265                 270

Val Asn Thr Pro Gln Thr Gly Thr Ala Ala Asn Gly Gln Ser Ala
        275                 280                 285

Gln Asp Leu Asp Gln Leu Leu Gly Gly Leu Leu Lys Gly Leu Glu
            290                 295                 300

Ala Thr Leu Lys Asp Ala Gly Gln Thr Ala Thr Asp Val Gln Ser Ser
305                 310                 315                 320
```

```
Ala Ala Gln Ile Ala Thr Leu Leu Val Ser Thr Leu Leu Gln Gly Thr
            325                 330                 335

Arg Asn Gln Ala Ala Ala
            340

<210> SEQ ID NO 3
<211> LENGTH: 30
<212> TYPE: DNA
<213> ORGANISM: Artificial Sequence
<220> FEATURE:
<223> OTHER INFORMATION: Synthetic primer derived from Pseudomonas
      syringae pv. Syringae 61

<400> SEQUENCE: 3
aaaatctaga atgcagagtc tcagtcttaa                                      30

<210> SEQ ID NO 4
<211> LENGTH: 30
<212> TYPE: DNA
<213> ORGANISM: Artificial Sequence
<220> FEATURE:
<223> OTHER INFORMATION: Synthetic primer derived from Pseudomonas
      syringae pv. Syringae 61

<400> SEQUENCE: 4
aaaagtcgac tcaggctgca gcctgattgc                                      30

<210> SEQ ID NO 5
<211> LENGTH: 32
<212> TYPE: DNA
<213> ORGANISM: Artificial Sequence
<220> FEATURE:
<223> OTHER INFORMATION: Synthetic primer derived from the reported
      PSPAL1 promoter

<400> SEQUENCE: 5
ggggtctaga attgatacta aagtaactaa tg                                   32

<210> SEQ ID NO 6
<211> LENGTH: 32
<212> TYPE: DNA
<213> ORGANISM: Artificial Sequence
<220> FEATURE:
<223> OTHER INFORMATION: Synthetic primer derived from the reported
      PSPAL1 promoter

<400> SEQUENCE: 6
ttggaagctt agagatcatt acgaaattaa gg                                   32

<210> SEQ ID NO 7
<211> LENGTH: 29
<212> TYPE: DNA
<213> ORGANISM: Artificial Sequence
<220> FEATURE:
<223> OTHER INFORMATION: Synthetic primer derived from the reported
      PSPAL1 promoter

<400> SEQUENCE: 7
ctaaaagctt ggtcatgcat ggttgcttc                                       29
```

DISEASE-RESISTANT PLANTS AND METHOD OF CONSTRUCTING THE SAME

This is a Continuation of application Ser. No. 10/363,832 filed on Sep. 11, 2003, now U.S. Pat. No. 7,525,014, and for which priority is claimed under 35 U.S.C. §120. application Ser. No. 10/363,832 is the National Stage Application of PCT International Application No. PCT/JP01/07785 filed on Sep. 7, 2001, which claims the benefit of priority of Japanese Application No. 271413/2000 filed on Sep. 7, 2000 under 35 U.S.C. §119. The contents of all of the aforementioned applications are incorporated herein by reference.

FIELD OF THE INVENTION

The present invention relates to methods for producing disease-resistant plants, gene expression cassettes for producing disease-resistant plants, and transgenic, disease-resistant plants produced by the method.

BACKGROUND OF THE INVENTION

Plant defense against pathogens differs in its mechanism from that observed in animals. For example, there is known in higher plants a hypersensitive response (HR) mechanism which involves a dynamic resistance reaction to pathogen invasion. When a pathogen invades a plant, plant cells at a site of invasion die in response, whereby pathogens are trapped locally. This reaction is known to be induced as a result of either an incompatible host-pathogen interaction or a non-host-pathogen interaction. Such cell suicide can be understood in terms of a localized, programmed cell death (Dangl et al.: Plant Cell 8: 1973-1807 (1996)). In addition to mechanism involving HR, other defense reactions, including generation of active oxygen species, reinforcement of a cell wall, production of phytoalexin and biosynthesis of defense-related proteins such as PR proteins, are also known (Hammond-Kosack and Jones: Plant Cell 8: 1773-1791 (1996)). Further, in addition to such localized defense responses, there is known to take place in many cases a defense reaction spreads whereby PR proteins accumulate also in non-infected parts of a plant, whereby resistance is imparted to the entire plant. This mechanism is referred to as systemic acquired resistance (SAR) and continues for several weeks or longer. As a result, the entire plant is made resistant to secondary infection (Sticher et al.: Annu. Rev. Phytopathol. 35: 235-270 (1997)).

A first reaction of a plant of switching on a highly organized defense reaction such as outlined above is the recognition by the plant of a molecule called an "elicitor" directly or indirectly produced by an invading pathogen. Additionally, complex signal cascades including the subsequent rapid generation of active oxygen species and reversible protein phosphorylation are considered to be important as initial reactions of the defense response (Yang et al.: Genes Dev. 11: 1621-1639 (1997)). There are a wide variety of elicitors, including so-called non-specific elicitors e.g. oligosaccharides which are products by degradation of cell wall components of many fungi including chitin/chitosan and glucan, or oligogalacturonic acids derived from a plant cell wall, variety-specific elicitors e.g. avirulence gene products of pathogens such as AVR 9 (Avr gene products), and elicitors with an intermediate specificity such as elicitin (Boller: Annu. Rev. Plant Physiol. Plant Mol. Biol. 46: 189-214 (1995)).

Harpin is a bacterium-derived protein elicitor which induces hypersensitive cell death in a non-host plant (Wei et al.: Science 257: 85-88 (1992), He et al.: Cell 73: 1255-1266 (1993)). Harpin (harpin$_{Ea}$) has been purified as a first bacterium-derived HR-inducing protein from *Erwinia amylovora* Ea321, a pathogen of pear and apple, and *Escherichia coli* transformed with a cosmid containing the hrp gene cluster, and an hrpN gene encoding Harpin has been cloned (Wei et al.: Science 257: 85-88 (1992)). Thereafter, harpin$_{pss}$ encoded by hrpZ gene has been identified and characterized from *Pseudomonas syringae* pv. *syringae* 61, a pathogen of a bean, by screening an *Escherichia coli* expression library with an activity of inducing HR to a tobacco leaf as an index (He et al.: Cell 73: 1255-1266 (1993), and Japanese Patent Application Domestic Announcement No. 1996-510127). The homology between these two harpins is low, and a relatively high homology is found only in 22 amino acids. Moreover, the role of a harpin in pathogenicity has not been made clear. In addition to these, as a third protein, PopA protein (which PopA encodes) is identified from *Pseudomonas solanacearum* GMI1000, a pathogen of a tomato, as a protein inducing HR to a non-host tobacco (Arlat et al.: EMBO. J. 13: 543-553 (1994)). Though PopA gene is located on the outside of hrp cluster, differing from hrpN and hrpZ, they are identical in that they are under the control of an hrp regulon. The above three proteins are glycine-rich, heat stable proteins, induce HR to a non-host tobacco and are secreted extracellularly at least in vitro in a manner of depending upon hrp protein. In addition to these are reported HrpW protein from *Pseudomonas syringae* pv. *tomato* DC3000 as a protein having the same function (Charkowski et al.: J. Bacteriol. 180: 5211-5217 (1998)), hrpZ$_{pst}$ and hrpZ$_{psg}$ proteins as harpin$_{pss}$ homologues (Preston et al.: Mol. Plant-Microbe. Interact. 8: 717-732 (1995)), and harpin$_{Ech}$ (Bauer et al.: Mol. Plant-Microbe. Interact. 8: 484-491 (1995)) and hrpN$_{ECC}$ protein (Cui et al.: Mol. Plant-Microbe. Interact. 9: 565-573 (1996)) as harpin$_{Ea}$ homologues.

It has been made apparent from studies upon various metabolic inhibitors that the formation of localized necrosis spots with harpin is not so-called necrosis due to the cytotoxicity of harpin but a cell death resulting from a positive response on the plant side (He et al.: Mol. Plant-Microbe. Interact. 7: 289-292 (1994), and He et al.: Cell 73: 1255-1266 (1993)), and this hypersensitive cell death is thought to be a type of programmed cell death (Desikan et al.: Biochem. J. 330: 115-120 (1998)). The addition of harpin$_{pss}$ into a cell culture of *Arabidopsis* induces a homologue of gp91-phox, a constituent of NADPH oxidase, which is thought to have an important role in the oxidative burst as an initial reaction of a disease-resistant reaction, (J. Exp. Bot. 49: 1767-1771 (1998)), and mitogen-activated protein (MAP) kinase (Desikan et al.: Planta. 210: 97-103 (1999)). Moreover, a harpin can impart systemic acquired resistance (SAR) to a plant. For example, SAR mediated by salicylic acid and an NIM gene can be induced to an *Arabidopsis* plant by artificially injecting harpin$_{Ea}$ into the plant cells (Dong et al.: The Plant J. 20: 207-215 (1999)), and Harpin$_{pss}$ can induce SAR to a cucumber and impart a wide spectrum of resistance to fungi, viruses and bacteria (Strobel et al.: Plant J. 9: 431-439 (1996)).

Thus, there are reports about artificially injecting or spraying purified harpin into a plant and analyzing the induction of a hypersensitive cell death and an acquired resistance reaction (Japanese Patent Application Domestic Announcement No. 1999-506938, Strobel et al.: Plant J. 9: 431-439 (1996), and Dong et al.: The Plant J. 20: 207-215 (1999)). However, there is no report about introducing a gene encoding an elicitor protein such as a harpin into a plant to produce a transgenic plant and analyzing it.

SUMMARY OF THE INVENTION

It has been anticipated that, when a gene encoding an elicitor protein such as harpin is introduced into a plant, the plant will express an elicitor protein at a certain amount, even in a normal state with no pathogen, or that it will also express an elicitor protein in a certain amount in organs other than those invaded with a disease, and as a result, various unintended reactions occur to prevent the plant from growing normally. The object of the present invention is therefore to provide a disease-resistant transgenic plant which has been transformed to induce a proper defense reaction, and to provide a method for producing the same.

The present inventors have engaged in studies assiduously, and as a result have found that a transgenic tobacco with hrpZ gene of *Psedomonas syringae* pv. *syringae* LOB2-1 introduced thereinto induces hypersensitive-response-like localized necrosis spots in response to the inoculation of a powdery mildew fungi (*Erysiphe cichoracearum*) to become resistant, which has led to the completion of the present invention. Surprisingly, a plant grew normally when cell-death-inducing harpin was expressed with a constitutive promoter (cauliflower mosaic virus 35S RNA gene promoter) capable of promoting expression in cells of the whole body. In addition, a hypersensitive cell-death-like reaction was induced only after inoculation with a pathogen. Further, the present inventors have found that a transgenic rice with the same hrpZ gene introduced thereinto becomes blast (*Magnaporthe grisea*)-resistant, thus showing the general-applicability of the present invention.

The present invention provides a transgenic, disease-resistant plant which has been transformed with an expression cassette comprising a promoter capable of promoting a constitutive, inducible, or organ- or phase-specific gene expression and a gene encoding an elicitor protein under the control of said promoter, wherein said plant is capable of effecting the constitutive, inducible, or organ- or phase-specific expression of the elicitor protein in an amount effective for inducing a defense reaction.

DETAILED DESCRIPTION OF THE INVENTION

The present invention also provides methods for producing transgenic, disease-resistant plants capable of effecting the constitutive, inducible, or organ- or phase-specific expression of an elicitor protein in an amount effective for inducing a defense reaction. Such methods comprise the steps of: (a) obtaining transgenic plant cells with expression cassettes comprising a promoter capable of promoting a constitutive, inducible, or organ- or phase-specific gene expression and a gene encoding an elicitor protein under the control of said promoter; and (b) regenerating a complete plant from said transgenic plant cell.

The present invention also provides expression cassettes capable of being employed for producing a transgenic, disease-resistant plants. Such expression cassettes comprise at least: (a) a promoter capable of promoting a constitutive, inducible, or organ- or phase-specific gene expression; and (b) a gene, under the control of said promoter, encoding an elicitor protein.

"Elicitor" is a general term used for substances inducing defense reactions in plants, and including heavy metal ions, and cell wall components of pathogens or plants, in addition to proteins. The term "elicitor" as used in the present specification refers to a protein elicitor unless otherwise specified.

The term "elicitor protein" as used in the present invention can be any protein capable of inducing a proper defense reaction in a plant to be transformed, and preferably a protein possessing a hypersensitive-response-inducing activity against pathogenic microorganisms. It includes harpin and a harpin-like protein having the same function as harpin. "Harpin" is a protein expected to be introduced into a plant in a manner of depending upon hrp gene though the Type III secretion mechanism, and includes, in addition to harpin$_{pss}$ (He et al.: Cell 73: 1255-1266 (1993), and Japanese Patent Application Domestic Announcement[kohyo] No. 510127/96), harpin$_{Ea}$ (Wei et al.: Science 257: 85-88 (1992), and Japanese Patent Application Domestic Announcement[kohyo] No. 506938/99), PopA (Arlat et al.: EMBO. J. 13: 543-553 (1994)), and hrpW protein (Charkowski et al.: J. Bacteriol. 180: 5211-5217 (1998). Additionally the protein possessing a hypersensitive-response-inducing activity can be, for example, (a) a protein consisting of the amino acid sequence of SEQ ID NO: 2; (b) a protein consisting of an amino acid sequence derived from the amino acid sequence of SEQ ID NO: 2 by deletion, substitution, addition or insertion of one or more amino acids, and possessing a hypersensitive-response-inducing activity; or (c) a protein consisting of an amino acid sequence being at least 50% (preferably at least 80%, more preferably at least 90%, and still more preferably at least 97%) homologous to the amino acid sequence of SEQ ID NO: 2, and possessing a hypersensitive-response-inducing activity. A protein consisting of the amino acid of SEQ ID NO: 2 is novel. Hence, the present invention provides one of the following proteins: (a) a protein consisting of the amino acid sequence of SEQ ID NO: 2; (b) a protein consisting of an amino acid sequence derived from the amino acid sequence of SEQ ID NO: 2 by deletion, substitution, addition or insertion of one or more amino acids, and possessing a hypersensitive-response-inducing activity; and (c) a protein consisting of an amino acid sequence being at least 97% homologous to the amino acid sequence of SEQ ID NO: 2, and possessing a hypersensitive-response-inducing activity (but known proteins themselves are excluded from the scope of the present invention).

By "Homology" referred to in connection with amino acid sequences in the present specification is meant a degree of identification of amino acid residues constituting each sequence between sequences to be compared. In homology, the existence of a gap(s) and the nature of an amino acid(s) are taken into consideration (Wilbur, Proc. Natl. Acad. Sci. USA 80: 726-730 (1983) and the like). To calculate homology, commercially available software such as BLAST (Altschul: J. Mol. Biol. 215: 403-410 (1990), and FASTA (Peasron: Methods in Enzymology 183: 63-69 (1990)) can be employed.

The description "deletion, substitution, addition or insertion of one or more amino acids" as used in the present specification in connection with an amino acid sequence in the means that a certain number of an amino acid(s) are substituted etc. by any well known technical method such as site-specific mutagenesis, or naturally. The number is, for example, up to ten, and is preferably from 3 to up to 5.

A gene encoding an elicitor protein to be employed in the expression cassette of the present invention can easily be isolated by methods well-known to those skilled in the art.

The gene encoding an elicitor protein can be, for example, (a) a DNA molecule consisting of the nucleotide sequence of SEQ ID NO: 1; (b) a DNA molecule consisting of a nucleotide sequence derived from the nucleotide sequence of SEQ ID NO: 1 by deletion, substitution, addition or insertion of one or more nucleotides, and encoding a protein possessing a hypersensitive-response-inducing activity; (c) a DNA molecule consisting of a nucleotide sequence being hybridizable with a DNA molecule consisting of the nucleotide sequence complementary to the nucleotide sequence of SEQ ID NO: 1 under stringent conditions, and encoding a protein possessing a hypersensitive-response-inducing activity; or (d) a DNA molecule consisting of a nucleotide sequence being at least 50% (preferably at least 80%, more preferably at least 90%, and still more preferably at least 97%) homologous to the nucleotide sequence of SEQ ID NO: 1, and encoding a protein possessing a hypersensitive-response-inducing activity. A DNA molecule consisting of the nucleotide sequence of SEQ ID NO: 1 is novel. Hence, the present invention also provides a gene consisting of one of the following DNA molecules: (a) a DNA molecule consisting of the nucleotide sequence of SEQ ID NO: 1; (b) a DNA molecule consisting of a nucleotide sequence derived from the nucleotide sequence of SEQ ID NO: 1 by deletion, substitution, addition or insertion of one or more nucleotides, and encoding a protein possessing a hypersensitive-response-inducing activity; (c) a DNA molecule consisting of a nucleotide sequence being hybridizable with a DNA molecule consisting of the complementary nucleotide sequence to the nucleotide sequence of SEQ ID NO: 1 under stringent conditions, and encoding a protein possessing a hypersensitive-response-inducing activity; or (d) a DNA molecule consisting of a nucleotide sequence being at least 50% homologous to the nucleotide sequence of SEQ ID NO: 1, and encoding a protein possessing a hypersensitive-response-inducing activity (but known genes themselves such as hrpZ gene of *Pseudomonas syringae* pv. *syringae* 61 are excluded from the scope of the present invention). To calculate homology in connection with nucleotide sequences, commercially available software can be employed.

By "deletion, substitution, addition or insertion of one or more nucleotides" in connection with a nucleotide sequence in the present specification is meant that a certain number of a nucleotide(s) are substituted etc. by a well-known technical method such as a site-specific mutagenesis or naturally. The number is, for example, up to ten, preferably from 3 to up to 5. By "stringent conditions" referred to in the present specification is meant hybridization conditions wherein the temperature is at about 40° C. or above and that the salt concentration is of about 6×SSC (1×SSC=15 mM sodium citrate buffer; pH: 7.0; 0.15 M sodium chloride; 0.1% SDS), preferably at about 50° C. or above, more preferably about 65° C. or above.

The promoter to be employed in the present invention can be any promoter capable of functioning as a promoter for a gene encoding an elicitor protein in a plant to be transformed. In the present invention, a promoter capable of promoting a constitutive, inducible, or organ- or phase-specific gene expression can be employed.

By "promoter promoting a constitutive gene expression (often referred to as a "constitutive promoter")" is meant a promoter whose organ specificity and/or phase specificity are (is) not high in connection with the transcription of the gene. Examples of the constitutive promoter include cauliflower mosaic virus 35S promoter, ubiquitin promoter (Cornejo et al.: Plant Mol. Biol. 23: 567-581 (1993)), actin promoter (McElroy et al.: Plant Cell 2: 163-171 (1990)), alpha tubulin promoter (Carpenter et al.: Plant Mol. Biol. 21: 937-942 (1993)) and Sc promoter (Schenk et al.: Plant Mol. Biol. 39: 1221-1230 (1999)). In a transgenic plant, the expression cassette promoting the constitutive expression of an elicitor protein includes, for example, a known promoter that is known as a constitutive promoter.

By "promoter promoting an inducible gene expression (often referred to as an "inducible promoter")" is meant a promoter which induces transcription by physical or chemical stimulation, such as light, disease, injury or contact with an elicitor. Examples of the inducible promoter include pea PAL promoter, Prp1 promoter (Japanese Patent Application No. 1998-500312), hsr203J promoter (Pontier et al.: Plant J. 5: 507-521 (1994)), EAS4 promoter (Yin et al.: Plant Physiol. 115: 437-451 (1997)), PR1b1 promoter (Tornero et al.: Mol. Plant. Microbe. Interact. 10: 624-634 (1997)), tap1 promoter (Mohan et al.: Plant Mol. Biol. 22: 475-490 (1993)) and AoPR1 promoter (Warner et al.: Plant J. 3: 191-201 (1993)). In a transgenic plant, the expression cassette promoting an inducible elicitor protein expression includes, for example, a known promoter known as an inducible promoter.

By "promoter promoting an organ-specific gene expression (often referred to as an "organ-specific promoter")" is meant a promoter giving, to the transcription of the gene, a specificity to an organ, such as a leaf, a root, a stem, a flower, a stamen and a pistil. Examples of the organ-specific promoter include a promoter promoting a high gene expression in green tissues of a photosynthesis-related gene, such as PPDK (Matsuoka et al.: Proc. Natl. Acad. Sci. USA 90: 9586-9590 (1993)), PEPC (Yanagisawa and Izui: J. Biochem. 106: 982-987 (1989) and Matsuoka et al.: Plant J. 6: 311-319 (1994)) and Rubisco (Matsuoka et al.: Plant J. 6: 311-319 (1994)). In a transgenic plant, the expression cassette promoting an organ-specific elicitor protein expression includes, for example, a known promoter that is known as an organ-specific promoter.

By "promoter promoting a phase-specific gene expression (often referred to as a "phase-specific promoter")" is meant a promoter giving, to the transcription of the gene, a phase specificity to a phase, such as a initial, middle and later growth phase. Examples of the phase-specific promoter include a promoter functioning specifically in aged leaves such as SAG12 promoter (Gan and Amashino: Science 270: 1986-1988 (1985)).

Vectors for sub-cloning each DNA fragment as a component of the expression cassette of the present invention can be simply prepared by connecting an intended gene into a vector for recombination (plasmid DNA) available in the art by any common technique. Specific examples of suitable vectors include plasmids derived from *Escherichia coli*, such as pBluescript, pUC18, pUC19 and pBR322, but are not limited only to these plasmids.

As a vector for introducing the expression cassette of the present invention into a plant to be transformed, a vector for transforming plants can be used. The vectors for plants are not particularly limited, so far as they are capable of expressing the concerned gene and producing the concerned protein in a plant cell, and examples thereof include pBI221, pBI121 (both being manufactured by Clontech) and vectors derived therefrom. In addition, for the transformation of a monocotyledonous plant in particular, there can be exemplified pIG121Hm, pTOK233 (both by Hiei et al.: Plant J. 6: 271-282 (1994)), pSB424 (Komari et al.: Plant J. 10: 165-174 (1996)), superbinary vector pSB21 and vectors derived therefrom. A recombination vector having the expression cassette of the present invention can be constructed by introducing a gene encoding an elicitor protein into any of these known vectors (if required, a promoter region being recombined) by a procedure known well to those skilled in the art. For example, a recombinant vector having an expression cassette comprising a constitutive promoter and hrpZ gene can be constructed by integrating hrpZ gene into superbinary vector pSB21. A recombinant vector having an expression cassette comprising an inducible promoter and hrpZ gene can be constructed by removing the existing promoter from the above recombinant vector and integrating an inducible promoter in place.

A plant-transforming vector preferably comprises at least a promoter, a translation initiator codon, a desired gene (a DNA sequence of the invention of the present application or a part thereof), a translation termination codon and a terminator. Moreover, it may comprise a DNA molecule encoding a signal peptide, an enhancer sequence, a non-translation region on the 5' side and the 3' side of the desired gene and a selection marker region as appropriate. Examples of marker genes include antibiotic-resistant genes such as tetracyclin, ampicillin, kanamycin or neomycin, hygromycin or spectinomycin; and genes such as luciferase, β-galactosidase, β-glucuronidase(GUS), green fluorescence protein (GFP), β-lactamase and chloramphenicol acetyl transferase (CAT).

As methods for introducing a gene into a plant can be mentioned a method employing an *agrobacterium* (Horsch et al.: Science 227: 129 (1985), Hiei et al.: Plant J. 6: 271-282 (1994)), a leaf disc method (Horsch et al.: Science 227: 1229-1231 (1985), an electroporation method (Fromm et al.: Nature 319: 791 (1986)), a PEG method (Paszkowski et al.: EMBO. J. 3: 2717 (1984)), a micro-injection method (Crossway et al.: Mol. Gen. Genet. 202: 179 (1986)) and a minute substance collision method (McCabe et al.: Bio/Technology 6: 923 (1988)), but any method for introducing a gene into a desired plant may be employed without any particular limitation. Of these methods for transfection, a method comprising transferring a vector into an *agrobacterium* by mating and then infecting a plant with the *agrobacterium* is preferred. Methods for infection is also well-known to those skilled in the art. Examples include a method comprising damaging a plant tissue and infecting it with a bacterium; a method comprising infecting an embryo tissue (including an immature embryo) of a plant with the bacterium; a method comprising infecting with a callus; a method comprising co-culturing protoplasts and the bacterium; and a method comprising culturing a fragment of a leaf tissue together with the bacterium (leaf disc method).

Successfully transformed cells can be selected from other cells by employing an appropriate marker as an index or examining the expression of a desired trait. The transformed cell can further be differentiated employing a conventional technique to obtain a desired transgenic plant.

Analysis of the resultant transformant can be performed by employing various methods that are well-known to those skilled in the art. For example, oligonucleotide primers can be synthesized according to the DNA sequence of the introduced gene, and the chromosome DNA of the transgenic plant can be analyzed by PCR employing the primers. In addition, the analysis can be performed on the basis of the existence of mRNA corresponding to the introduced gene and the existence of the protein expression. Moreover, the analysis can be performed on the basis of the appearance of the plant (for example, in the case of transformation with a gene encoding a protein capable of inducing localized necrosis spots, the presence of localized necrosis spots, or the size, number and the like of the localized necrosis spots), disease resistance (for example, the existence of resistance or its degree upon contacting the plant with a pathogen) and the like.

In the transgenic plant of the present invention, a constitutive, inducible, or organ- or phase-specific expression of an elicitor protein in an amount effective for inducing a defense reaction can be achieved. The amount effective for inducing a defense reaction is such an amount that the expressed elicitor protein can induce at least a localized defense-related reaction (for example, induction of a hypersensitive cell death (localized necrosis)) to the plant. Preferably, the amount is such that the defense reaction extends to the whole body of the plant, and as a result, the whole plant becomes resistant (systemic acquired disease-resistant). Moreover, preferably, the amount is not so large that causes death of the localized tissue having the necrosis spots as a result of the localized necrosis spots becoming too large.

Moreover, in the transgenic plant of the present invention, an elicitor protein is preferably expressed in an amount which, while being effective for inducing a defense reaction in response to stimulation such as the invasion of a pathogen, does not, under normal conditions, remarkably prevent the growth of the plant due to the negligible or low expression, if any. For example, in the case of employing harpin$_{pss}$ as an elicitor protein, usually no harpin$_{pss}$ is expressed, or is expressed only in an amount that does not allow localized necrosis spots to cause the death of the organ, and preferably it is expressed in an amount that induces a hypersensitive response at the time of the invasion of a pathogen. Further, it is preferably expressed in such an amount that, even if a pathogen invades to cause harpin$_{pss}$ to accumulate, localized necrosis spots are hardly observable by the naked eye, but the whole body acquires a systemic disease-resistance.

In order to induce such a proper defense reaction, for example, a promoter capable of promoting an inducible gene expression is employed. Hence, in one embodiment of the present invention, an inducible promoter and a harpin gene are combined.

In addition, a proper defense reaction can be accomplished not only in the case of employing an inducible promoter but also in the case of employing a constitutive promoter. Hence, in another embodiment of the present invention, a constitutive promoter and a harpin gene are used in combination. In this embodiment, as a mechanism of the occurrence of a proper defense reaction, it is considered that an elicitor protein, for example, harpin$_{pss}$, is recognized at the outside of cell membranes or on the cell wall of plant cells, and hence, harpin$_{pss}$ accumulating in cytoplasm is not recognized by plant cells until degradation of cells occurs due to invasion of fungus, and as a result, the hypersensitive response appears after the inoculation of the pathogen or it is deduced that there exists a further factor which is related to the inoculation of a pathogen in the mechanism of the occurrence of the elicitor activity of harpin$_{pss}$.

The transgenic plants of the present invention include a transgenic, powdery mildew-resistant tobacco which has been transformed with an expression cassette comprising a constitutive or inducible promoter and a gene, under the control of said promoter, encoding an elicitor protein such as harpin$_{pss}$, or a transgenic, blast-resistant rice which has been transformed with an expression cassette comprising a constitutive promoter and a gene, under the control of the promoter, encoding an elicitor protein such as harpin$_{pss}$.

It is thought that the present invention can be applied to plants other than rice and tobacco described in the examples to be described later. Examples of such plants include, as crops, wheat, barley, rye, corn, sugar cane, sorghum, cotton, sunflower, peanut, tomato, potato, sweet potato, pea, soybean, azuki bean, lettuce, cabbage, cauliflower, broccoli, turnip, radish, spinach, onion, carrot, eggplant, pumpkin, cucumber, apple, pear, melon, strawberry and burdock; and, as ornamental plants, *arabidopsis thaliana*, petunia, chrysanthemum, carnation, *saintpaulia* and *zinnia*. The "transgenic plants" referred to in the present invention include not only transgenic plants (T$_0$ generation) obtained by obtaining a transgenic plant cell according to the method of the present invention and regenerating, from said plant cell, a complete plant, but also later-generation (T$_1$ generation and the like) plants obtained from said transgenic plants so far as the disease-resistant trait is contained. In addition, the "plants" referred to in the present invention include, unless otherwise specified, in addition to plants (individuals), seeds (including germinated seeds and immature seeds), organs or parts thereof (including a leaf, a root, a stem, a flower, a stamen, a pistil and pieces thereof), a plant culture cell, a callus and a protoplast.

The diseases analyzed in the following examples are tobacco powdery mildew and rice blast, but as other diseases of tobacco there can be mentioned wildfire, bacterial wilt and TMV; and as other diseases of rice there can be mentioned sheath blight disease and bacterial leaf blight disease. According to the method for producing a disease-resistant plant of the present invention, it is possible to impart resistance in plants to these diseases.

EXAMPLES

Example 1

Cloning of HrpZ Gene

A pair of primers for amplifying the open leading frame of hrpZ gene were synthesized in reference to the nucleotide sequence of the reported hrpZ gene of *Pseudomonas syringae* pv. *syringae* 61 (He et al.: Cell 73: 1255-1266 (1993)), and Japanese Patent Application Domestic Announcement[Kohyo] No. 1996-510127):

```
                                       (SEQ ID NO: 3)
Hrp1:   AAA ATC TAG AAT GCA GAG TCT CAG TCT TAA (SEQ ID NO: 4)
Hrp2:   AAA AGT CGA CTC AGG CTG CAG CCT GAT TGC
```

Employing these primers, PCR was performed with a DNA molecule of a cosmid clone containing an hrp cluster derived from *Pseudomonas syringae* pv. *syringae* LOB2-1 (a casual agent for bacterial blight of lilac) (Inoue and Takikawa: J. Gen. Plant Pathol. 66: 238-241 (2000)) as a template. PCR was performed under the following conditions: the amount of a reaction solution: 20 µl; each primer: 0.5 µM; dNTP: 0.2 mM; 1×ExTaq buffer; ExTaq DNA polymerase (from Takara Shuzo): 1 U; once at 95° C. for 5 minutes, then 30 cycles at 94° C. for 30 seconds, at 60° C. for 30 seconds and at 72° C. for 2 minutes, and once at 72° C. for 10 minutes. The PCR product was ligated to a vector pCR2.1 (from Invitrogen) using Takara ligation kit (from Takara Shuzo) and transformed into an *Escherichia coli* TB1 strain. As a result of determining the entire nucleotide sequence of the PCR product, it consisted of 1029 bp in the length, longer than the reported hrpZ gene (He et al.: Cell 73:1255-1266 (1993)) by three bases (one amino acid), and showed a homogoly of 96.7% in nucleotides and a homology of 96.5% in amino acids. The reason that the nucleotide sequences are not completely the same is thought to be due to a variation among the pathover. The nucleotide sequence of the cloned hrpZ gene is shown in SEQ ID NO: 1 and the deduced amino acid sequence obtained therefrom is shown in SEQ ID NO: 2, respectively.

Example 2

Expression in an *Escherichia coli* and Production of an Antibody

The above plasmid with an hrpZ gene integrated into pCR2.1 was digested with restriction enzymes BamHI and SalI, and was subjected to electrophoresis on 0.7% agarose to separate a fragment of about 1.1 kb. This fragment was ligated to an expression vector pQE31 (from QIAGEN) digested with the same enzymes and transformed into *Escherichia coli* M15 strain. The thus obtained *Eschrichia coli* was cultured in an LB medium in the presence of 1 mM of IPTG at 37° C., harpin$_{pss}$ was accumulated as insoluble fraction. Since this protein showed poor adsorption to a nickel resin adsorbent, the purification of harpin$_{pss}$ was conducted in the following procedure. The *Eschrichia coli* M15 strain having the pQE31 vector with the hrpZ gene integrated thereinto was cultured in 2 ml of an LB medium containing 100 mg/l of ampicillin and 25 mg/l of kanamycin at 37° C. overnight, and transferred into 250 ml of the LB medium and cultured for about three hours; then 1 mM of IPTG was added thereto and the culture was further conducted at 37° C. for 4 hours. Cells were collected by centrifugation, the insoluble fraction was dissolved in 4 ml of an eluation buffer (8 M urea, 0.1 M sodium dihydrogen phosphate, 0.01 M Tris, pH 8.0), and a supernatant liquid was obtained by centrifugation and subjected to electrophoresis on a 12.5% acrylamide gel containing 0.1% SDS, and then stained with Coomassie Brilliant Blue to cut a band appearing at around 40 kDa. The gel was cut into small pieces, and an elution buffer (1% SDS, 0.02 M Tris-HCl, pH of 8.0) was added thereto in an amount ten times the volume of the gel, and shaken for three days. The supernatant was transferred to a dialysis membrane with a cut off molecular weight of 6,000 to 8,000, and the dialysis was conducted with 80% acetone as an external liquid once for 4 hours and once overnight. The whole content in the dialysis tube was moved into an Eppendorf tube, subjected to centrifugation to discard the supernatant, and the pellet was dried to obtain a purified harpin$_{pss}$ preparation. 3 mg of the purified harpin$_{pss}$ was sent to Sawady Technology for the production of an antibody (anti-rabbit harpin$_{pss}$ serum).

Example 3

Construction of a Gene and Transformation of a Plant

The hrpZ gene integrated into pCR2.1 was excised from the vector by digestion with restriction enzymes XbaI and SacI (from Takara Shuzo). On the other hand, superbinary vector pSB21 (35S-GUS-NOS, Komari et al.: Plant J. 10: 165-174 (1996)) was digested with the same enzymes to remove the GUS gene, and the hrpZ gene was integrated thereinto. According to the above procedure, a construct named 35S-hrpZ (35S promoter-hrpZ gene-NOS terminator)

was constructed. The cauliflower mosaic virus 35S promoter is a promoter capable of constitutively promoting a high expression, and it is anticipated that rice and tobacco transformed with this construct will accumulate harpin$_{pss}$, the hrpZ gene product, in the whole body.

pSB21 was digested with restriction enzymes HindIII and XbaI to remove the 35S promoter, and a 0.9 kb fragment of corn PPDK promoter (Taniguchi et al.: Plant Cell Physiol. 41: 42-48 (2000)) was integrated thereinto. The resulting plasmid was digested with XbaI and SacI to remove the GUS gene, and then the above-described hrpZ XbaI-SacI fragment was inserted thereinto. Thus, PPDK-hrpZ (PPDK promoter-hrpZ gene-NOS terminator) was constructed. The corn PPDK promoter is a promoter capable of promoting a strong expression in photosynthesis organs such as mesophyl cells (Taniguchi et al.: Plant Cell Physiol. 41: 42-48 (2000)), and it is anticipated that rice plants transformed with this construct will accumulate harpin$_{pss}$, the hrpZ gene product, in green organs (leaves).

PAL promoter was cloned as below. Plasmid DNA was extracted from *agrobacterium* LBA4404 strain (gifted from Prof. Shiraishi of Okayama University) having a construct containing PSPAL1 (PSPAL1 promoter-GUS gene-NOS terminator) (Yamada et al.: Plant Cell Physiol. 35: 917-926 (1994), and Kawamata et al.: Plant Cell Physiol. 38: 792-803 (1997)). On the other hand, a reverse primer and two forward primers were designed on the basis of the nucleotide sequence of the reported PSPAL1 promoter (Patent: JP 1993153978-A 1 22-JUN-1993; TAKASAGO INTERNATL. CORP.):

```
PALRVXba:
                                    (SEQ ID NO: 5)
GGG GTC TAG AAT TGA TAC TAA AGT AAC TAA TG

PALFFHin:
                                    (SEQ ID NO: 6)
TTG GAA GCT TAG AGA TCA TTA CGA AAT TAA GG

PALFSHin:
                                    (SEQ ID NO: 7)
CTA AAA GCT TGG TCA TGC ATG GTT GCT TC
```

A promoter region (PAL-S) of about 0.45 kb in the upstream of the starting point of translation (about 0.35 kb at the upstream of the initiation point of transcription) was amplified by the combination of PALRVXba and PALFSHin, and a promoter region (PAL-L) of about 1.5 kb by the combination of PALRVXba and PALFFHin. The above-mentioned *agrobacteruium* plasmid DNA was used as a template and PCR was conducted with these primers. The reaction conditions of PCR were as below: reaction solution: 50 µl; each primer: 0.5 µM, dNTP: 0.2 mM; 1×ExTAq buffer, ExTAq DNA polymerase (from Takara Shuzo): 1 U; and the reaction was conducted once at 94° C. for three minutes, then 30 cycles at 94° C. for one minute, at 50° C. for one minute and at 72° C. for two minutes, and once at 72° C. for 6 minutes. A PCR product was cloned to vector pCRII (from Invitrogen).

Since the PsPAL1 promoter had a HinIII site at the upstream 142 bp from the starting point of translation, PAL-S was digested completely with restriction enzyme XbaI and then partially with HindIII to obtain a 0.45 kb of fragment from pCRII. The above mentioned pSB21 was digested with HindIII and XbaI to remove the 35S promoter, and PAL-S was integrated thereinto. In the pSB21 vector employed here the unique PvuII site existing in the basic structure had been removed, and, instead, a PvuII linker had been placed at the unique ECORI site (just after the Nos terminator). The plasmid with PAL-S integrated thereinto was further digested with XbaI and SacI to remove the GUS gene, and then the above mentioned 1.1 kb hrpZ XbaI-SacI1 fragment was inserted therein. PALS-hrpZ was constructed according to the above procedure. Next, PAL-L integrated into pCRII was digested with restriction enzymes XhoI and XbaI to take out a 1.45 kb PAL promoter, which was integrated into vector pSBII (Komari et al.: Plant J. 10: 165-174 (1996)) co-digested with the same enzymes. The formed plasmid was digested with XbaI and SmaI, and an XbaI-PvuII fragment of PALS-hrpZ (hrpZ-NOS terminator) was inserted therein. In this manner, PALL-hrpZ was produced. The PAL promoter promotes a low-level expression constitutively, but it is a promoter strongly induced with a pathogen and an injury (Yamada et al.: Plant Cell Physiol. 35: 917-926 (1994), and Kawamata et al.: Plant Cell Physiol. 38: 792-803 (1997)), and it is anticipated that a tobacco plant transformed with PALS-hrpZ or PALL-hrpZ accumulates more harpin$_{pss}$ at the place of stress when these stresses occur. In this case, it is anticipated that more harpin$_{pss}$ will accumulate in the case of PALL relative to the case of PALS.

Figure 1:
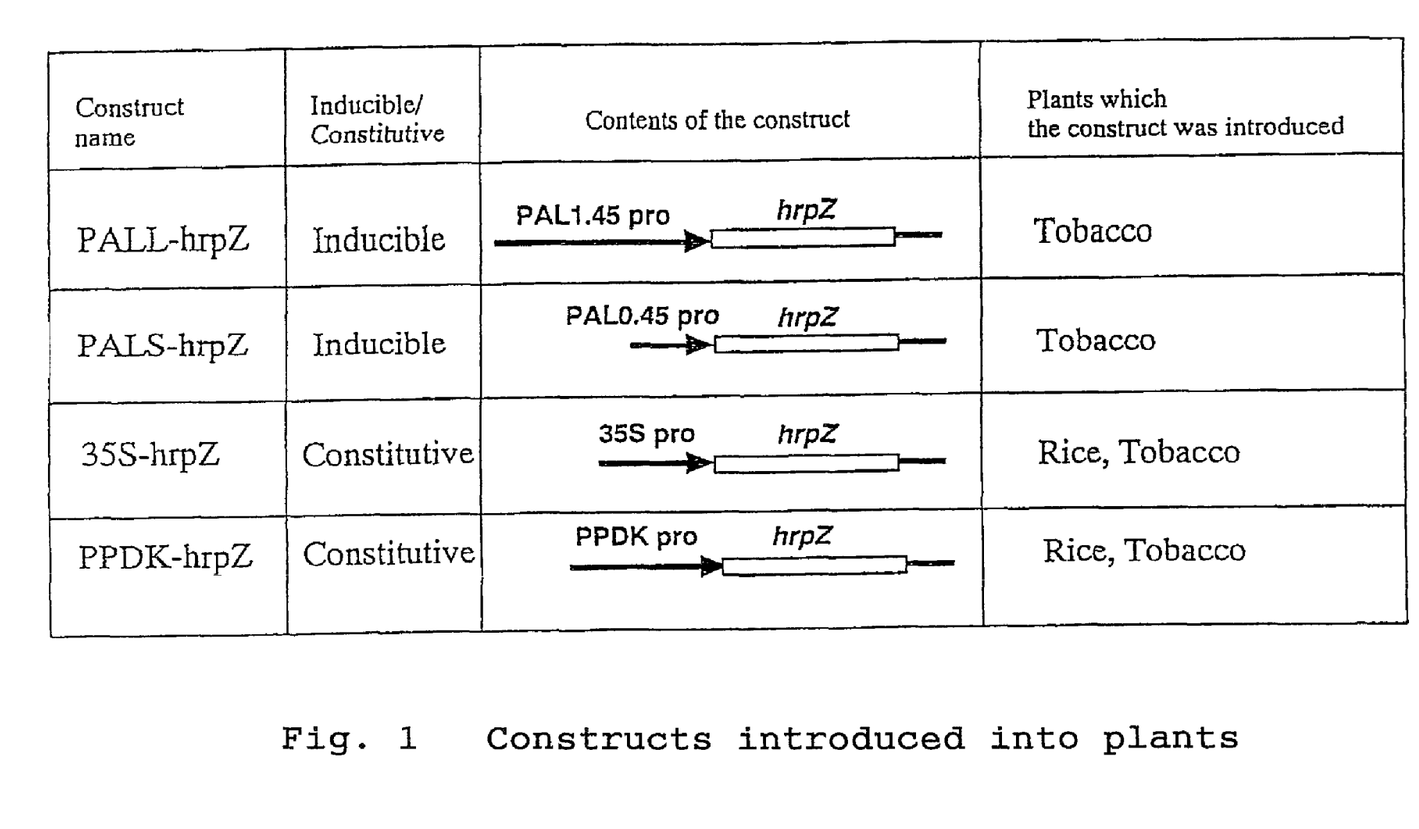
FIG. 1 shows the constructs constructed and introduced into plants in the present invention.

According to the tri-parental mating system, of *Escherichia coli* LB392 strain containing the thus produced four constructs 35S-hrpZ, PALS-hrpZ, PALS-hrpZ and PALL-hrpZ (summarized in FIG. 1), *agrobacterium* LBA4404 strain containing a vector pSB4U with a selection marker gene integrated thereinto (corn ubiquitin promoter-hygromycin-resistant gene (hptII)-NOS terminator) and *Escherichia coli* HB101 containing a helper plasmid pRK2013, the hrpZ gene containing construct was introduced into an *agrobacterium* utilizing homologous recombination.

The transformation of a tobacco was performed by the leaf disc method (Horsch et al.: Science 227: 1229-1231 (1985)). A leaf of tobacco variety SR1 grown in a greenhouse was sterilized by treatment with ethanol for 30 seconds and with antiformin diluted 5 times for 5 minutes, and after it was cleaned with sterilized water twice, it was cut into one-centimeter squares, and an *agrobacterium* suspension was inoculated thereto. The concentrations of hygromycin at the time of induction and selection of a transfected shoot and at the time of rooting were 50 or 100 mg/ml and 0 or 50 mg/ml, respectively. For the transformation of rice, immature-embryo-derived cali of varieties of paddy rice, *Tsukinohikari*, and *Koshihikari* were transformed employing *agrobacterium* according to the method of Hiei et al.: Plant J. 6: 271-282 (1994).

Example 4

Analysis of Transformants (1) Transgenic Tobacco 15 individuals of the re-generated plant were obtained from 35S-hrpZ, 10 individuals were from PALS-hrpZ and 16 individuals were from PALL-hrpZ. There was observed no remarkable difference between the constructs in transformation efficiency. Western analysis was performed on the primary generation ($T_0$) of the transformant, and Western analysis and disease assays were performed on the self-pollinated next generation ($T_1$).

1) Western Analysis of $T_0$ Generation

Figure 2:
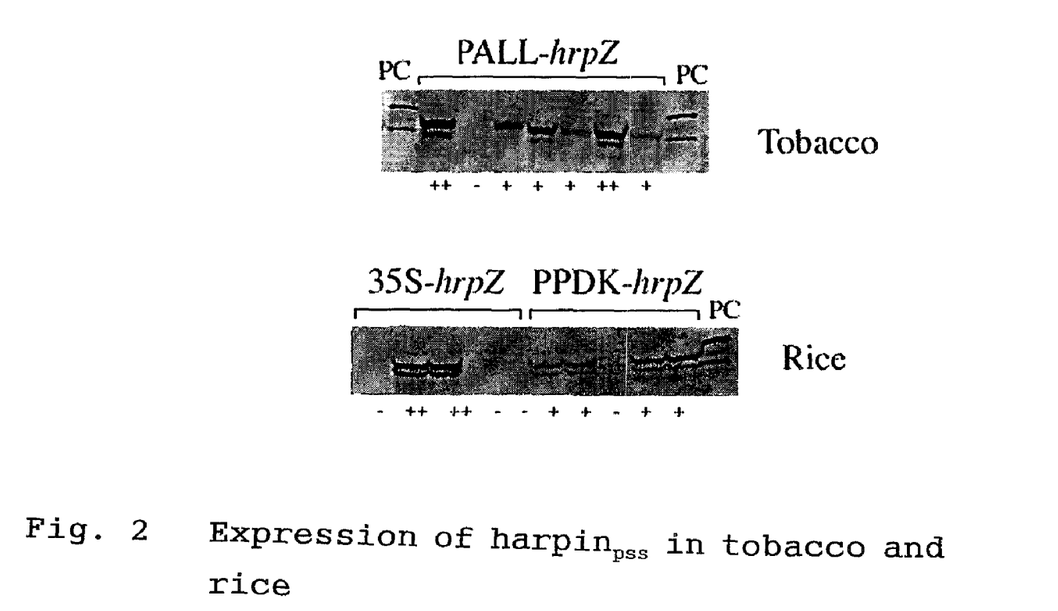
FIG. 2 is a photograph showing exemplary of the detection results using Western analysis for harpin$_{pss}$ accumulation in transgenic tobacco and rice of the $T_0$ generation. PC represents harpin$_{pss}$ expression in *Escherichia coli* as a control.

2×2 cm of a leaf of a transgenic tobacco of the 4 or 5 leaf stage and 2×2 cm of a leaf of a non-transgenic tobacco (SR1) were pulverized in 0.1 M HEPES-KOH pH 7.6 buffer in a mortar. The supernatant liquid after centrifugation with 15000 g for 10 minutes was made a protein sample. The amount of the protein was determined with a Bio-Rad Protein Assay kit (from BIO-RAD). About 20 µg of the protein was fractioned by the SDS-PAGE method according to the method of Laemmni et al. (Nature 227: 680-685 (1970)), on 12.5% PAGEL (from ATTO). After electrophoresis, the protein bands on the gel were transferred to a PVDF membrane (from Millipore). The PVDF membrane was placed in a 1×TBS buffer containing 0.5% skim milk for 30 minutes, and shaken in the same buffer containing 1/1000 (v/v) of anti-harpin$_{pss}$ serum at room temperature overnight. As a secondary antibody was employed an anti-goat rabbit IgG peroxidase labeled conjugate (from MBL) or an anti-goat rabbit IgG alkaline phosphatase conjugate (from BIO-RAD) at the concentration of 1/1000 (v/v). As color development systems were employed HRP Color Development Reagent (from BIO-RAD), alkaline phosphatase substrate kit II (from Vector Laboratories). The amounts of the protein expressed were calculated by comparison with the color development of the harpin$_{pss}$ sample of a known concentration, by using a densitometer (model GS-670, from BIO-RAD). Some of the results of the Western analysis of the $T_0$ generation is shown in FIG. 2, and the whole results are summarized in Table 1.

The expression level is shown in four stages (+++, ++, +, −), which show 0.1% or more of the total soluble proteins (+++), 0.05 to 0.1% (++), 0.05% or less (+) and below the detection limitation (−) in the amount of expression, respectively. This is true also in Tables 2, 3 and 4 to be described later.

TABLE 1

Results of the Western Analysis of the Tobacco $T_0$ Generation

| Construct | Number of re-generated individuals | Expression level of Harpin$_{pss}$[a] | | | |
|---|---|---|---|---|---|
| | | − | + | ++ | +++[b] |
| PALS-hrpZ | 10 | 1 | 8 | 1 | 0 |
| PALL-hrpZ | 16 | 2 | 10 | 4 | 0 |
| 35S-hrpZ | 15 | 6 | 2 | 1 | 6 |
| SR1 | | 3 | 0 | 0 | 0 |

[a]Each numerical value shows the number of individuals showing each expression level.
[b]The expression level of harpin$_{pss}$ is shown in four stages (+++: particularly high expression, ++: high expression, +: moderate to poor expression, −: below the detection limitation).

In the case of the constructs having a PAL promoter, the accumulation of harpin$_{pss}$ was detected in 80% or more of individuals. As anticipated, PALL had a larger proportion of high-expression individuals (++) than PALS. On the other hand, in the case of the construct having a 35S promoter, though no accumulation of harpin$_{pss}$ was detected in 6 individuals of the 15 individuals, high-expression individuals were obtained in 7 individuals, near half of the total individuals. Besides, a very high expression (+++) was shown in 6 individuals. Interestingly, no morphological change was observed in the organ of any of a leaf, a stem, a root or a flower of these high-expression individuals, and seed fertility was normal in almost all of them.

2) Western Analysis of the $T_1$ Generation and Disease Resistance Assay

Reaction to powdery mildew fungus (*Erysiphe cichoracearum*) was analyzed in about 8 lines of KH1-2 (PALS-hrpZ), KC6-7 (PALL-hrpZ), KC8-1 (PALL-hrpZ), KK1-1 (35S-hrpZ), KK3-8 (35S-hrpZ), KK4-2 (35S-hrpZ), KK4-3 (35S-hrpZ), KK7-6 (35S-hrpZ), in which the amount of harpin$_{pss}$ accumulated was high in the $T_0$ generation.

Figure 3:
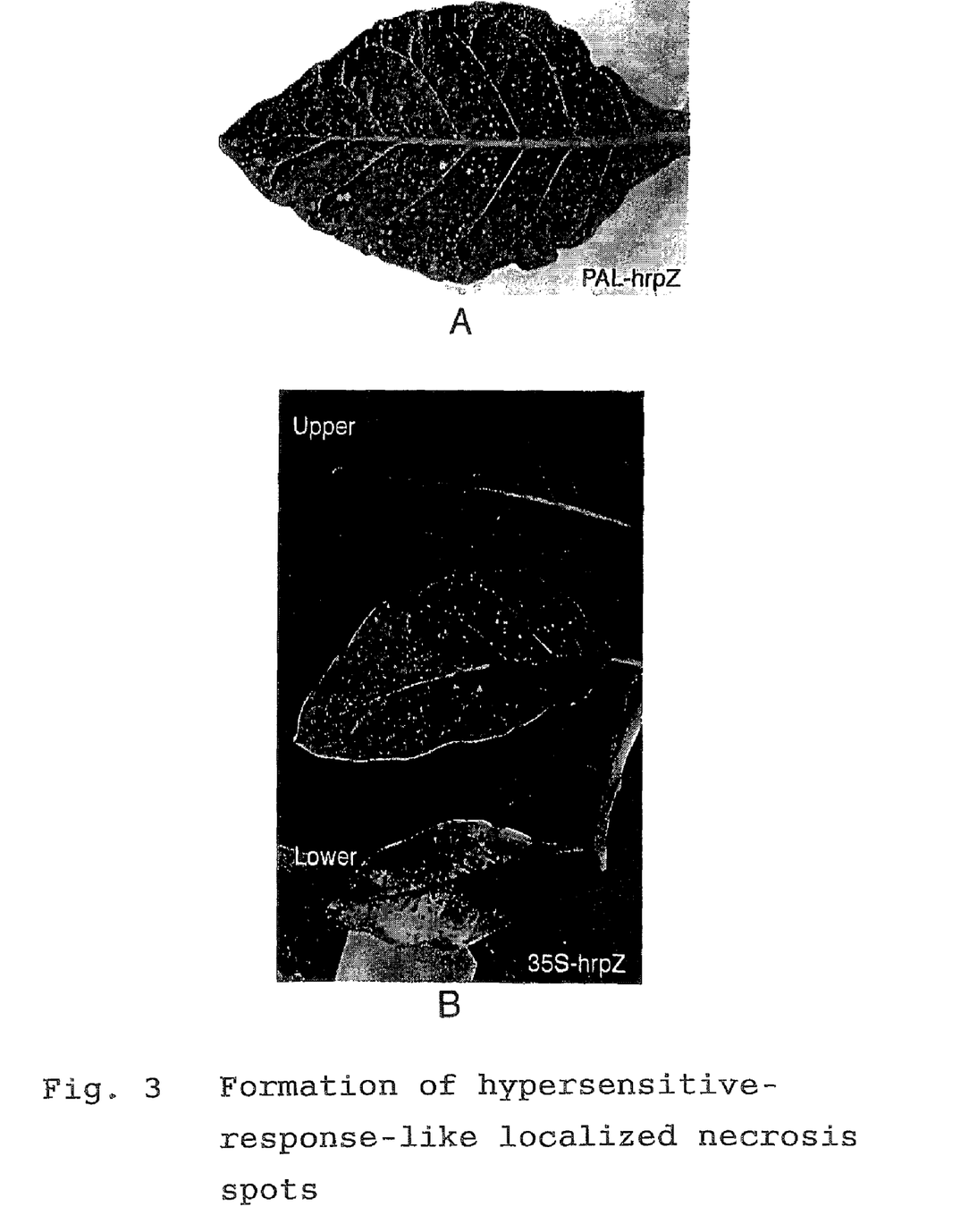
FIG. 3 is a photograph showing the appearances of localized necrosis spots occurring in a transgenic tobacco of the $T_1$ generation. A: PALL-hrpZ-introduced individual (5th day after inoculation, harpin expression level: ++), B: 35S-hrpZ-introduced individual (7th day after inoculation, harpin expression level: ++)

Tobacco individuals in which harpin$_{pss}$ was accumulated at a high level in the $T_0$ generation were selected, and seeds of self-pollinated next generation ($T_1$) thereof were obtained. The seeds were sowed and observed for about two months, but no visual morphological change was observed for this period; they grew normally in the same manner as the $T_0$ generation, and no hypersensitive response was observed on the surface of a leaf. Then, powdery mildew fungi were sprayed to inoculate upon the $T_1$ generation of the transgenic tobacco of the 4 or 5 leaf stage and a disease resistance assay was performed. About 2 L of a suspension of powdery mildew fungi spores (1.4×10$^6$ spores/ml) was spray-inoculated to 244 recombinants and 41 original individuals. As a result, hypersensitive-response-like localized necrosis spots were induced onto a lower leaf of the recombinant 4 or 5 days after inoculation (FIG. 3A, B). Surprisingly, not only in the case of the PAL-hrpZ constructs but also in the case of the 35S-hrpZ constructs employing a constitutive promoter, specific localized necrosis spots were induced after the pathogen infection (FIG. 3B). The expression frequency of localized necrosis spots on the 5th day after the inoculation was about 5% in the non-transformants, but the frequency was from 6 to 14 times grater in the 35S-hrpZ construct (30 to 71%), from 4 to 5 times greater in the PAL-hrpZ constructs (20 to 27%) (Table 2), and thereafter, in the case of the PAL-hrpZ constructs, the number of local necrosis spots gradually increased. This was assumed to be due to the response of the PsPAL1 promoter to *Erysiphe cichoracearum*. Though the amount of harpin$_{pss}$ accumulated and the degree of the formation of localized necrosis spots tended to be positively correlative (Table 3), there were some exceptional transformants in which no accumulation of harpin$_{pss}$ was detected at least in our Western analysis but localized necrosis spots occurred.

Figure 4:
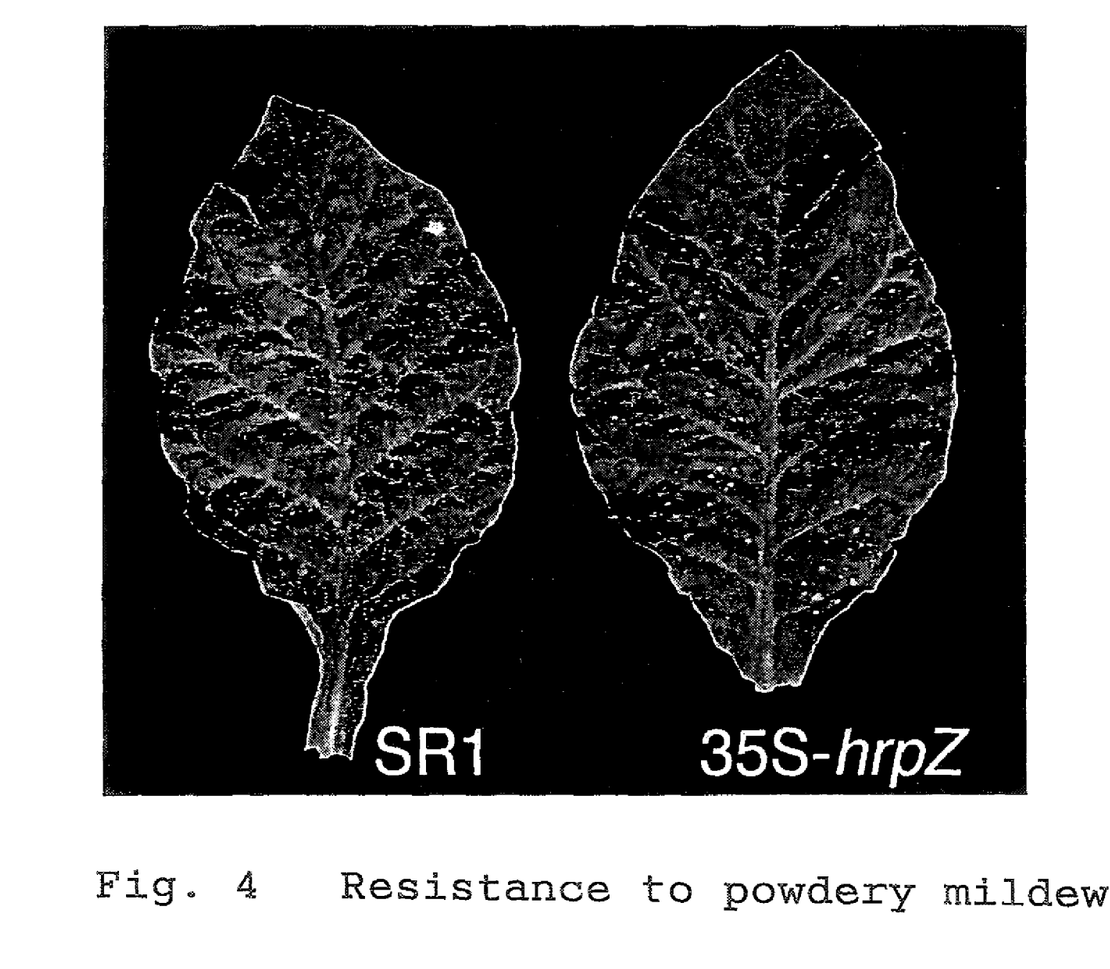
FIG. 4 is a photograph showing the resistance of a transgenic tobacco of the $T_1$ generation against powdery mildew. (Right: 35S-hrpZ-introduced individual, harpin expression level: ++, Left: SRI as a control, 11th day after inoculation in both)

Next, in order to examine whether the localized necrosis spots having occurred after the powdery mildew infection were related to disease resistance, the symptom of powdery mildew on the 11th day after the inoculation thereof was examined. As a result, while there existed no individual in which the spread of powdery mildew hyphae was prevented in the non-transformants, from 15 to 57% individuals in the case of 35S-hrpZ constructs and from 13 to 18% individuals in the case of PAL-hrpZ constructs showed apparently less significant symptom as compared to the non-transformants (FIG. 4, Table 2). The prevention of that the spread of powdery mildew was observed not only in leaves with localized necrosis spots but also in middle or upper leaves with no localized necrosis spots, and this is thought to be due to systemic acquired resistance (SAR). As a result of observing the hyphae of powdery mildew by cotton blue dyeing, the hyphae of powdery mildew extended sharply and spread around the surface in infested leaves of the SR1 of the original line as a control, whereas, though haustorium is formed on the surface of a leaf in the transformants, the spreading of hyphae was prevented and stopped halfway. The promoters employed in the present studies are 35S promoter (constitutive) and PAL promoter (inducible); and it was found that when 35S promoter was employed instead of PAL promoter, the frequency of localized necrosis spots was higher, and it was further found that at least according to examination on the 11th day after inoculation, more individuals with a strong disease resistance were obtained (Table 2). However, it was observed that, in the case of employing the 35S promoter, the localized necrosis spots formed in response to the pathogen became larger (occupying 10% or more of the leaf area) in some individuals, and as a result, lower leaves died out. In addition, inversely, in some individuals with harpin$_{pss}$ accumulated therein, localized necrosis spots were not observable by the naked eye (Table 2), but some of such individuals had resistance to powdery mildew (of individuals with—of localized necrosis spots in Table 2, individuals of the number in parentheses; the amount of harpin$_{pss}$ expressed is ++ in all). This is thought to be probably due to the occurrence of a hypersensitive response in very small range, and it is possible that a disease-resistant plant with a high practicability can be obtained by the selection of such individuals. According to the fact that no localized necrosis spot occurred without the invasion of the pathogen even in the case where the transcription of hrpZ gene was controlled with a constitutive promoter, it is possible to deduce that, since harpin$_{pss}$ was recognized on the outside of a transmembrane or cell wall of plant cells, probably harpin$_{pss}$ accumulated in cytoplasm was not recognized for plant cells till the degradation of cells due to the invasion of the fungi, and as a result, it caused a hypersensitive response after the inoculation of the pathogen. Another possibility may be that the elicitor activity of harpin$_{pss}$ requires the existence of some other factors derived from the pathogen or the plant, induced by the inoculation of the pathogen.

performed on the primary generation ($T_0$) of the transformation and individuals with a high expression were selected.

Protein was extracted from the regenerated transgenic rice (*Tsukinohikari*) in the same manner as in the example of the tobacco and subjected to Western analysis. The results of Western analysis of the $T_0$ generation are shown in Table 4.

TABLE 2

Relationship among the Amount of harpin$_{pss}$ Accumulated, the Formation of Localized Necrosis Spots and Disease Resistance of the Tobacco $T_1$ Generation

| Line Name | Construct | Expression level ($T_0$) | Number of individuals analyzed ($T_1$) |
|---|---|---|---|
| KH1-2 | PALS-hrpZ | ++ | 18 |
| KC6-7 | PALL-hrpZ | ++ | 43 |
| KC8-1 | PALL-hrpZ | ++ | 44 |
| KK1-1 | 35S-hrpZ | +++ | 23 |
| KK3-8 | 35S-hrpZ | +++ | 33 |
| KK4-2 | 35S-hrpZ | ++ | 35 |
| KK4-3 | 35S-hrpZ | +++ | 7 |
| KK7-6 | 35S-hrpZ | +++ | 41 |
| SR1 | (control) | − | 41 |

| Line Name | Number of individuals with localized necrosis spots (Number of individuals with less progress of disease spots) | | | | Rate of individuals with localized necrosis spots (5th day after inoculation) | Rate of individuals with less progress of disease spots (11th day after inoculation) |
|---|---|---|---|---|---|---|
| | +++ | ++ | + | −[a] | | |
| KH1-2(PALS) | 0 | 0 | 5(3) | 13(0) | 27% | 16% |
| KC6-7(PALL) | 0 | 1(1) | 8(6) | 34(1) | 20% | 18% |
| KC8-1(PALL) | 0 | 1(0) | 11(5) | 32(1) | 27% | 13% |
| KK1-1(35S) | 0 | 0 | 7(3) | 16(1) | 30% | 17% |
| KK3-8(35S) | 0 | 2(0) | 11(5) | 20(0) | 39% | 15% |
| KK4-2(35S) | 1(1) | 4(3) | 15(6) | 15(0) | 57% | 28% |
| KK4-3(35S) | 0 | 3(3) | 2(1) | 2(0) | 71% | 57% |
| KK7-6(35S) | 1(1) | 4(4) | 18(4) | 18(1) | 56% | 24% |
| SR1(control) | 0 | 0 | 2(0) | 39(0) | 5% | 0% |

[a]The degree of localized necrosis spots is shown in four stages (+++: very high, ++: high, +: low, −: nil).

TABLE 3

Relationship between the Expression level of Harpin$_{pss}$ and the Number of Localized Necrosis Spots in the Tobacco $T_1$ Generation

| Expression level of harpin$_{pss}$[a] (Western analysis) | Degree of localized necrosis spots[b] | | | | Incidence of localized necrosis spots |
|---|---|---|---|---|---|
| | +++ | ++ | + | − | |
| +++ | 1 | 4 | 19 | 19 | 56% |
| ++ | 0 | 5 | 32 | 77 | 32% |
| + | 1 | 6 | 18 | 38 | 40% |
| − | 0 | 1 | 5 | 18 | 25% |
| SR1 | 0 | 0 | 2 | 39 | 5% |

[a]The expression level of harpin$_{pss}$ is shown in four stages (+++: particularly high expression, ++: high expression, +: moderate to poor expression, −: below the detection limit) (SR1, −).
[b]The degree of localized necrosis spots is shown in four stages (+++: great many, ++: many, +: few, −: nil).

(2) Transgenic Rice

1) Western Analysis of the $T_0$ Generation

Harpin$_{pss}$ was introduced into a rice variety, *Tsukinohikari*. 35 individuals of the regenerated plant were obtained from the 35S-hrpZ construct, and 26 individuals of the regenerated plant were obtained from the PPDK-hrpZ construct. There was observed no remarkable difference between the constructs in transformation efficiency. Western analysis was

TABLE 4

Results of the Western Analysis of the $T_0$ Generation of Rice (*Tsukinohikari*)

| Construct | Number of regenerated individuals | Expression level of harpin$_{pss}$[a] | | | |
|---|---|---|---|---|---|
| | | − | + | ++ | +++[b] |
| 35S-hrpZ | 35 | 17 | 5 | 13 | 0 |
| PPDK-hrpZ | 26 | 9 | 13 | 4 | 0 |

[a]Each numerical value shows the number of individuals showing each expression level.
[b]The Expression level of harpin$_{pss}$ is shown in four stages (+++: particularly high expression, ++: high expression, +: moderate to poor expression, −: below the detection limit).

In the case of the rice (*Tsukinohikari*), similar to the case of the tobacco, individuals with a high-expression of harpin$_{pss}$ were obtained (see also FIG. 2). In the case of a construct having a 35S promoter, the accumulation of harpin$_{pss}$ was detected in about half of the individuals, and the rate of high-expression individuals (++) was about one-third or more of the whole. Also, in the case of a PPDK promoter the accumulation of harpin$_{pss}$ was detected in about two-thirds of the individuals, and of them, 4 individuals showed a high expression. Interestingly, no morphological change was observed in the organ of any of a leaf, a root or a flower of these high-expression individuals. And seed fertility was normal in almost all of them, and $T_1$ seeds of high-expression individuals could be obtained.

2) Western Analysis of the $T_0$ Generation and the Disease Resistance Assay of the $T_1$ Generation Next, harpin$_{pss}$ was introduced into *Koshihikari*, one of the most important varieties of rice of Japan. The results of the Western analysis of the $T_0$ generation are shown in Table 5.

TABLE 5

Results of the Western Analysis of the $T_0$ Generation of Rice (Koshihikari)

| Construct | Number of regenerated individuals | Expression level of harpin$_{pss}$[a] | | | |
|---|---|---|---|---|---|
| | | − | + | ++ | +++[b] |
| 35S-hrpZ | 78 | 18 | 33 | 21 | 6 |
| PPDK-hrpZ | 27 | 7 | 13 | 7 | 0 |

[a]Each numerical value shows the number of individuals showing each expression level.
[b]The expression level of harpin$_{pss}$ is shown in four stages (+++: amount of accumulation of 0.5% or more to the total soluble leaf proteins, ++: amount of accumulation of from 0.1 to 0.5%, +: amount of accumulation of from 0.01 to 0.1%, −: below the detection limit).

Of the individuals of the $T_0$ generation with the 35S-hrpZ construct introduced thereinto, four individuals showing a large amount (+++ in Table 5) of the accumulation of harpin$_{pss}$ (hrp5-8, hrp23-5, hrp24-1, hrp42-9) were selected, and their vulnerability to rice blast in the $T_1$ generation was examined. The seed fertility of the selected four high-expression individuals was normal, and many self-fertilized seeds could be obtained. $T_1$ seeds were sowed in a seedling case with culture soil in a manner of 8 seeds×2 rows, cultivated in a greenhouse, and subjected to a disease assay at the 4.8 to 5.2 leaf stage. As a rice blast fungus (*Magneporthe grisea*) was employed race 007. For inoculation, a conidium formed by culturing the blast fungi on an oatmeal sucrose agar medium at 28° C. under dark condition and then, after the spread of the fungi, at 25° C., irradiating near ultraviolet light for three days was employed. The inoculation of the blast fungi was performed by spray-inoculating 30 ml of a suspension adjusted to $1.5 \times 10^5$ condia/ml in 0.02% Tween 20 per three seedling cases. The spray-inoculated rice was held in a moistening incubator (SLPH-550-RDS, manufactured by Nippon Medical & Chemical Instruments Co. Ltd.) for 24 hours after the inoculation at 25° C. at a humidity of 100%, and then transferred into the greenhouse. The conditions of the greenhouse were set at 25° C. under light conditions for 16 hours, and at 22° C. under dark conditions for 8 hours. The evaluation of disease resistance was performed by visually counting the number of progressive disease spots on the 5th leaf at 6th day after the inoculation, said leaf being the topmost development leaf at the time of inoculation. Significant differences among the results were evaluated according to the Mann-Whitney U test.

As a result, though no localized necrosis spot due to the inoculation of the blast fungi was observed, the average number of progressive disease spots was reduced by 24 to 38% relative to the control *Koshihikari* in three lines (hrp5-8, hrp42-9, hrp23-5) out of the four lines of the harpin$_{pss}$-introduced rice. Moreover, this reduction was statistically significant (Table 6). The above results show that the disease resistance of rice could be increased by the introduction of harpin$_{pss}$.

TABLE 6

Results of the Disease Test against Rice Blast of the Four Lines of Harpin$_{pss}$ - Intorduced Rice ($T_1$ Generation)

| Strain | Number of tested individuals | Number of average progressive disease spots[a] (standard error) | Significant Test[b] |
|---|---|---|---|
| hrp5-8 | 16 | 9.3 (±1.0) | significant (significance level 1%,) |
| hrp23-5 | 21 | 11.4 (±1.3) | significant (significance level 5%) |
| hrp24-1 | 20 | 14.4 (±1.4) | No significant difference |
| hrp42-9 | 14 | 9.4 (±1.4) | significant (significance level 1%) |
| Koshihikari | 64 | 15.0 (±0.7) | — |

[a]Results of the 5th leaf on the 6th day after inoculation
[b]Significant difference to Koshihikari in the Mann-Whitney U test As a result of the present invention, it has become apparent for the first time that disease resistance can be imparted to a plant by connecting a gene encoding harpin to a constitutive promoter or an inducible promoter and introducing the gene into the plant. This harpin-introduced plant is thought to be useful for explicating the function of harpin as a protein elicitor, and also for explicating the mechanism of localized or systemic acquired resistance. In addition, it is revealed that the production of a harpin-introduced resistant plant, which has been thought to be difficult without the use of an inducible promoter, can sufficiently be realized by employing a constitutive promoter, and the extension of the application range of the present approach can be shown. The present invention shows that a method for producing a disease-resistant plant by integrating a DNA sequence encoding a harpin into an expression cassette comprising a sequence of an appropriate constitutive, or organ- or phase-specific promoter capable of functioning in a plant cell, or a promoter induced with stress or pests, and a sequence of a terminator capable of functioning in a plant cell, and introducing it into the plant cell to obtain a regenerated individual is a useful and effective approach in view of genetic engineering.

The invention claimed is:

1. A transgenic, disease-resistant plant which has been transformed with an expression cassette comprising:
   a promoter that promotes a constitutive gene expression; and
   a gene, under the control of said promoter, encoding a harpin;
   wherein transformed cells in the transgenic plant effect the constitutive expression of the harpin in an amount effective for inducing a defense reaction, and,
   wherein the harpin is a protein consisting of an amino acid sequence being at least 90% homologous to the amino acid sequence of SEQ ID NO: 2, and possessing a hyper-sensitive-response-inducing activity.

2. A transgenic, disease-resistant plant which has been transformed with an expression cassette comprising:
   a promoter that promotes a constitutive gene expression; and a gene, under the control of said promoter, encoding a harpin; wherein transformed cells in the transgenic plant effect the constitutive expression of the harpin in an amount effective for inducing a defense reaction, and,
   wherein said gene encoding the harpin is a DNA molecule consisting of a nucleotide sequence being at least 90% homologous to the nucleotide sequence of SEQ ID NO: 1, and encoding a protein possessing a hypersensitive-response-inducing activity.

3. A method for producing a transgenic, disease-resistant plant containing transformed cells that effect a constitutive expression of a harpin in an amount effective for inducing a defense reaction, comprising the steps of:
   (i) obtaining a transgenic plant cell with an expression cassette comprising a promoter capable of promoting a constitutive gene expression and a gene, under the control of said promoter, encoding a harpin; and
   (ii) regenerating a plant from said transgenic plant cell, wherein the harpin is a protein consisting of an amino acid sequence being at least 90% homologous to the amino acid sequence of SEQ ID NO: 2, and possessing a hyper-sensitive-response-inducing activity.

4. A method for producing a transgenic, disease-resistant plant containing transformed cells that effect a constitutive expression of a harpin in an amount effective for inducing a defense reaction, comprising the steps of:
   (i) obtaining a transgenic plant cell with an expression cassette comprising a promoter capable of promoting a constitutive gene expression and a gene, under the control of said promoter, encoding a harpin; and
   (ii) regenerating a plant from said transgenic plant cell, wherein said gene encoding the harpin is [selected from: (a) a DNA molecule consisting of a nucleotide sequence being hybridizable with a DNA molecule consisting of the complementary nucleotide sequence to the nucleotide sequence of SEQ ID NO: 1 under a condition of 65° C., 6×SSC, and encoding a protein possessing a hypersensitive-response-inducing activity; and (b)] a DNA molecule consisting of a nucleotide sequence being at least 90% homologous to the nucleotide sequence of SEQ ID NO: 1, and encoding a protein possessing a hypersensitive-response-inducing activity.

5. The transgenic, disease-resistant plant according to claim 1, wherein the harpin protein consists of an amino acid sequence at least 97% homologous to the amino acid sequence of SEQ ID NO: 2.

6. The transgenic, disease-resistant plant according to claim 2, wherein the DNA molecule consists of a nucleotide sequence at least 97% homologous to the nucleotide sequence of SEQ ID NO: 1.

7. The method according to claim 3, wherein the harpin protein consists of an amino acid sequence at least 97% homologous to the amino acid sequence of SEQ ID NO: 2.

8. The method according to claim 4, wherein the DNA molecule consists of a nucleotide sequence at least 97% homologous to the nucleotide sequence of SEQ ID NO: 1.

* * * * *